(12) United States Patent
Park et al.

(10) Patent No.: US 7,777,091 B2
(45) Date of Patent: Aug. 17, 2010

(54) POLYURETHANE FOAM DRESSING WITH IMPROVED MOISTURIZATION

(75) Inventors: Jong-wook Park, Seoul (KR);
 Hyun-jung Kim, Kyunggi-do (KR);
 Kab-keun Kim, Kyunggi-do (KR);
 Doo-hee Yoon, Kyunggi-do (KR)

(73) Assignee: Biopol Co., Ltd., Kyunggi-do (KR)

( * ) Notice: Subject to any disclaimer, the term of this patent is extended or adjusted under 35 U.S.C. 154(b) by 276 days.

(21) Appl. No.: 11/627,651

(22) Filed: Jan. 26, 2007

(65) Prior Publication Data

US 2008/0146983 A1 Jun. 19, 2008

(30) Foreign Application Priority Data

Dec. 19, 2006 (KR) .................. 10-2006-0130194

(51) Int. Cl.
 *A61F 13/00* (2006.01)
 *A61K 9/70* (2006.01)
 *C08J 9/00* (2006.01)

(52) U.S. Cl. .................... 602/43; 424/443; 604/304; 521/50

(58) Field of Classification Search ............ 602/41–43, 602/46–48, 56; 424/400, 443, 445–447, 424/472, 473; 604/304–308; 521/67, 65, 521/50

See application file for complete search history.

(56) References Cited

U.S. PATENT DOCUMENTS 3,800,792 A * 4/1974 McKnight et al. ............ 602/50
3,978,855 A * 9/1976 McRae et al. ................ 602/46
4,538,603 A * 9/1985 Pawelchak et al. ........... 602/56

(Continued)

FOREIGN PATENT DOCUMENTS

EP 0 335 669 A 10/1989

(Continued)

OTHER PUBLICATIONS

Park et al. (2002) J Korean Soc. Plast. Reconstr. Sur., 29(4):297-301, Medifoam® (Hydrophilic Polyurethane Foam).

(Continued)

*Primary Examiner*—Kim M. Lewis
*Assistant Examiner*—Tarla R Patel
(74) *Attorney, Agent, or Firm*—Swanson & Bratschun, L.L.C.

(57) ABSTRACT

The present invention relates to a polyurethane foam dressing material with improved moisturizing rate. More precisely, the present invention relates to a hydrophilic dressing material in which a wound contact layer (10) having a sponge structure composed of multiple open cells (12) and pores (15) passing through the cells (12) is laminated with a protective film (20). The lamination is characteristically performed at 150~250° C. under a pressure of preferably 0.25~1 kgf/cm², the moisturizing rate of the wound contact layer (10) is 300~1200% and the pore area (membrane opening) takes 10~35% of the total cell area.

The polyurethane foam dressing material of the present invention prevents the invasion of foreign materials, releases absorbed exudation after changing it into water vapor or arresting the absorbed exudation inside the foam to maintain constant moisturizing, has excellent exudation absorption capacity, has a wound healing effect resulting from not adhering to a wound, is easy to change, and enhances the wound healing effect by maintaining optimum moisturizing conditions resulting from the improved moisturizing rate.

9 Claims, 4 Drawing Sheets

U.S. PATENT DOCUMENTS

| | | | |
|---|---|---|---|
| 4,664,662 A | 5/1987 | Webster | |
| 4,704,113 A | 11/1987 | Schoots | |
| 5,064,653 A | 11/1991 | Sessions et al. | |
| 5,065,752 A | 11/1991 | Sessions et al. | |
| 5,254,301 A | 10/1993 | Sessions et al. | |
| 5,445,604 A | 8/1995 | Lang | |
| 5,489,262 A | 2/1996 | Cartmell et al. | |
| 5,501,661 A | 3/1996 | Cartmell et al. | |
| 5,503,847 A | 4/1996 | Queen et al. | |
| 5,571,529 A * | 11/1996 | Cheong | 424/445 |
| 5,830,932 A | 11/1998 | Kay | |
| 6,207,875 B1 * | 3/2001 | Lindqvist et al. | 602/46 |
| 6,326,410 B1 * | 12/2001 | Cheong | 521/67 |
| 6,486,378 B1 * | 11/2002 | Areskoug et al. | 602/41 |
| 6,881,875 B2 * | 4/2005 | Swenson | 602/46 |
| 2002/0062097 A1 | 5/2002 | Simpson | |
| 2004/0018227 A1 * | 1/2004 | Park et al. | 424/445 |

FOREIGN PATENT DOCUMENTS

| | | |
|---|---|---|
| GB | 2 290 031 A | 12/1995 |
| KR | 1020010008533 | 2/2001 |
| KR | 2002-0046619 A | 6/2002 |
| KR | 340981 B | 6/2002 |
| KR | 553078 | 6/2005 |
| WO | WO 00/78369 A1 | 12/2000 |

OTHER PUBLICATIONS

Lim et al. (2003) J Korean Burn Soc., 6(1):45-51, Foam Dressing Material.

Office Action issued Oct. 19, 2009 in U.S. Appl. No. 10/533,123.

* cited by examiner

POLYURETHANE FOAM DRESSING WITH IMPROVED MOISTURIZATION

RELATED APPLICATIONS

This application claims priority to Korean Application Serial No. 10-2006-0130194, filed Dec. 19, 2006, which is specifically incorporated herein by reference in its entirety.

TECHNICAL FIELD

The present invention relates to a polyurethane foam dressing material with improved moisturizing rate. More precisely, the present invention relates to a hydrophilic dressing material in which a wound contact layer, having a sponge structure composed of multiple open cells and pores that make a tunnel from cell to cell, is laminated with a protective film. The lamination is characteristically performed at 150~250° C. under a pressure of 0.25~1 kgf/cm$^2$, the moisturizing rate of the wound contact layer is 300~1200%, and the pore area (membrane opening) takes 10~35% of the total cell area.

The polyurethane foam dressing material of the present invention has the advantages of maintaining desired moisturizing conditions by blocking the invasion of foreign materials, releasing absorbed exudation to the outside after changing it into water vapor or arresting the absorbed exudation inside the foam, having a wound healing effect owing to its excellent exudation absorption without adhering to the wound, ease of dressing replacement, particularly promoting wound healing by maintaining optimum moisturizing conditions due to the improved moisturizing, and preventing contamination of clothes or sheets by avoiding exudation release due to an external force.

BACKGROUND ART

Once the skin has a wound, a huge amount of exudation is generated, which is called the 'inflammatory phase', then the proliferative phase occurs, in which granulation takes place, and finally the growing phase occurs in which newly generated skin becomes firm as the wound heals. The most important factor in the process of wound healing is to minimize the inflammatory phase by quickly absorbing exudation generated in the early inflammatory phase and to maintain proper moisturizing conditions during the growing phase to provide various cell growth factors (PDGF, TGF-β, EGF, FGF, VEGF, IGF, etc) or cytokines (IL-1, IL-6, IL-8, TNF, etc) to accelerate wound healing by helping cell migration and proliferation. It is preferable to use a dressing material that does not adhere to the wound.

The conventional gauze dressing absorbs wound exudate easily, but at the same time has the disadvantages of not-defending itself against infection by bacteria, keeping the wound area dry which delays recovery, and difficulty in changing dressings because it adheres to the wound, possibly damaging nascent tissues and causing pain. In the early treatment phase, a lot of exudate is generated so the dressing has to be changed frequently (for example, several times a day). As an alternative to overcome the disadvantages of the conventional gauze dressing, various obstructive dressing materials have been developed, but these new dressings are expensive, lack adequate absorption, and cannot regulate their water vapor permeability. Thus, the obstructive dressing materials are only applied to some specific types of wounds.

The obstructive dressing materials in use are films, hydrocolloids, hydrogels, polyurethane foams, etc. Particularly, hydrocolloids, hydrogels and polyurethane foams are favored because of their high treatment effect.

U.S. Pat. No. 5,503,847 and No. 5,830,932 describe a hydrocolloid dressing material which is composed of an adhesive composition layer, a hydrocolloid layer that absorbs impact and exudation, and a film layer that prevents the invasion of bacteria and impurities.

The hydrocolloid dressing material absorbs a small amount of wound exudate to form a gel and is able to provide humid conditions and maintain the pH as weakly acidic for a long time to prevent the disturbance of tissues and promote cell growth. However, water vapor permeability and exudation absorption are not satisfactory. During the change or removal of the dressing, the gel adheres to the wounded area and remains there, requiring secondary treatment to eliminate the residue. Thus, this dressing is not suitable for application to a wounded area that generates a large amount of exudate.

U.S. Pat. No. 5,501,661 and No. 5,489,262 describe a hydrogel dressing material. According to these descriptions, the hydrogel dressing material contains a non-permeable polymer film coated with hydrogel. The polymer film prevents dehydration or dryness of the hydrogel, and the hydrogel layer absorbs exudation by adhering to a wounded area and maintains humid conditions to accelerate wound healing. However, this dressing material is not suitable for application to a severe wound that generates a lot of exudation because of its low water vapor permeability and water absorptiveness. Excessive absorption of the dressing material deforms the dressing material itself, thereby making it difficult to change the dressing, and causes infection of normal tissues.

U.S. Pat. No. 5,445,604 and No. 5,065,752 describe a hydrophilic polyurethane foam dressing material having a triple layer structure in which both sides of the polyurethane foam are laminated with a film. Particularly, a wound contact layer film, which is laminated to prevent the huge wound contact layer pores from adhering to the wounded area, is designed to have a hole through which exudation is absorbed into the wound contact layer. However, exudation and blood cannot be completely absorbed from the wounded area, which generates blood clots on the area. Because of the generated blood clots, wound healing is retarded or the dressing adheres to the wound, and nascent tissues might also adhere to the dressing through the huge mechanically made pores, making it difficult to change the dressing and resulting in a dot shaped scar. When this dressing material is applied to a wound generating lots of exudation, the dressing has to be changed frequently because of the insufficient absorptiveness per unit area and the patient's clothes or sheets have to be changed often because exudation flows out through the dressing due to external forces owing to its weak moisturizing rate. In addition, the dryness around the wound or dryness of the wounded area itself when applied on a wound generating less exudation is another problem of this dressing material (J Korean Soc. Plast. Reconstr. Sur., Vol. 29, No. 4, 297-301, 2002; J Korean Burn Soc., Vol. 6, No. 1, 45-51, 2003).

U.S. Pat. No. 5,064,653 and No. 5,254,301 also describe a hydrophilic polyurethane foam dressing material. According to these descriptions, the dressing material has a triple layer structure in which a polyurethane foam produced by in situ reaction of a hydrophilic isocyanate-capped polyether prepolymer with a hydrotrope, water, an adjuvant and a wetting agent is laminated with films by two-part adhesive, which used to be added during continuous line foaming. Hydrophilicity and moisturizing rate have been improved by applying a hydrotrope and a wetting agent on the wound contact layer. However, the dressing material is still not suitable for operation wounds which produce a lot of exudation including blood, because excessive exudation is not absorbed in the dressing material and flows out through the wound contact layer to the patient's clothes or a sheet. In addition, the remaining blood generates blood clots on the wounded area, retarding wound healing, and the pore of the wound contact layer is bigger than a human cell so re-generated tissues adhere to the dressing, making it difficult to change the dressing (J Korean Burn Soc., Vol. 6, No. 1, 45-51, 2003).

The alternative to overcome the above mentioned problems has been proposed by the present inventors and described in Korean Patent No. 553078. According to the description, the polyurethane foam dressing material having a double-layer structure, in which an absorption layer having a water absorptiveness of 400~2,000 weight % is laminated with a protective film having a water vapor permeability of 200~1,500 g/m$^2$·day, is a ground-breaking development in wound healing. However, it still has a problem with regard to dryness around the wounded area when it is applied on a wound generating less exudation. Thus, a novel dressing material needs to be developed with an improved moisturizing rate that enables a hydrogel-like effect after absorbing exudation to provide comfortable humid conditions.

DISCLOSURE OF THE INVENTION

It is an object of the present invention, in order to solve the above problems, to provide a polyurethane foam dressing material with improved moisturizing rate, which is characterized by the ability to prevent the invasion of foreign materials, releasing absorbed exudation as water vapor or arresting it inside the foam to maintain humid conditions, the promotion of wound healing owing to its excellent exudation absorptiveness and non-adhesion to the wound contact layer, ease of dressing change, and accelerated wound healing by maintaining optimum humidity due to the improved moisturizing rate.

To achieve the above object, the present invention provides a hydrophilic dressing material in which a wound contact layer (10) having a sponge structure composed of multiple open cells (12) and pores (15) passing through the cells (12) is laminated with a protective film (20). The lamination is performed at 150~250° C. at a pressure of 0.25~1 kgf/cm$^2$, the moisturizing rate of the wound contact layer (10) is 300~1200%, and the pore area (membrane opening) takes 10~35% of the total cell area.

If the temperature for the lamination is lower than 150° C., the lamination of the protective film layer on the polyurethane foam absorption layer will not be successful. On the contrary, if the temperature is higher than 250° C., a color change will be observed in the polyurethane foam absorption layer.

If the pressure for the lamination is lower than 0.25 kgf/cm$^2$, the lamination of the protective film layer on the polyurethane foam absorption layer will not be successful. On the other hand, if the pressure is higher than 1 kgf/cm$^2$, the membrane opening will be increased in the polyurethane foam absorption layer, resulting in the decrease of moisturizing rate.

The mean diameter of the open cells (12) is preferably 50~300 μm and the mean diameter of the pores (15) is 5~85 μm.

If the mean diameter of the open cells is more than 330 μm, the moisturizing rate will be significantly decreased. If the mean diameter of the open cells is less than 10 μm, exudation absorption will be decreased and the absorption speed will also be very slow, resulting in a pool of exudation from incomplete elimination of wound exudation.

If the mean diameter of the pores is more than 85 μm, human cells migrate into the dressing material which causes the dressing to adhere to the wound and re-injures the wound during dressing change. If the mean diameter of the pores is less than 5 μm, clean elimination of the wound exudation will be difficult.

The preferable content of the open cells in the wound contact layer (10) is 20~80%.

If the open cells take more than 80% of the wound contact layer, the moisturizing rate will be significantly decreased, making it difficult to ensure humid conditions around the wounded area. If the open cells take less than 20% of the wound contact layer, exudation absorption will be significantly decreased.

The preferable density of the wound contact layer (10) is 0.15~0.45 g/cm$^3$.

If the density is more than 0.45 g/cm$^3$, the percentage of the open cells will be lowered to at best 20%, which decreases exudation absorption. If the density is less than 0.15 g/cm$^3$, the percentage of the open cells will be at least 80%, which means the moisturizing rate will drop significantly and the humidity around the wound will be poor.

The water absorptiveness of the wound contact layer (10) is preferably 400~2,000 weight %.

If the water absorptiveness is higher than 2,000 weight %, the inside structure of the foam requires a cell diameter of at least 300 μm and 90% open cells. If this is the case, the moisturizing rate of the dressing material will be significantly reduced and the humidity around the wound will be poor. If the water absorptiveness is less than 400 weight %, frequent dressing changes will be required.

Herein, the wound contact layer (10) is prepared by the steps of mixing 40~70 weight % of a polyurethane prepolymer with 15~45 weight % of a foaming agent, 5~35 weight % of a cross-linking agent, 0.1~2 weight % of a surfactant and 0.5~15 weight % of an adjuvant with stirring; pour-foaming the mixture in a mold to prepare a polyurethane foam; and slicing thereof.

The polyurethane prepolymer herein is preferably synthesized from an isocyanate (1~4 mol) and a polyetherpolyol (0.15~2 mol).

The isocyanate herein can be selected from a group consisting of isophoronediisocyanate, 2,4-toluenediisocyanate and its isomer, diphenylmethanediisocyanate, hexamethylenediisocyanate, lysinediisocyanate, trimethylhexamethylenediisocyanate, bis(2-isocyanateether)-fumarate, 3,3'-dimethyl-4,4'-diphenylmethanediisocyanate, 1,6-hexanediisocyanate, 4,4'-biphenylenediisocyanate, 3,3'-dimethylphenylenediisocyanate, p-phenylenediisocyanate, m-phenylenediisocyanate, 1,5-naphthalenediisocyanate, 1,4-xylenediisocyanate and 1,3-xylenediisocyanate. Particularly, diphenylmethanediisocyanate, 2,4-toluenediisocyanate and its isomer, p- henylenediisocyanate, isophoronediisocyanate and hexamethylenediisocyanate are more preferred.

The polyethylenepolyol can be prepared by mixing a ethyleneoxide/propyleneoxide random copolymer having at least three hydroxyl groups, a molecular weight of 3,000~6,000 and an ethyleneoxide content of 50~80% with a polypropyleneglycol having at least two hydroxyl groups and a molecular weight of 1,000~4,000 at the ratio of 30:70, and it is more preferred to select the above ethyleneoxide/propyleneoxide random copolymer alone as the polyethylenepolyol. However, other isocyanate compounds and polyols can be added to regulate the physical properties of the product.

The foaming agent can be selected from a group consisting of chlorofluorocarbon (CFC-141b), methylenechloride and distilled water, with distilled water being more preferred.

The cross-linking agent can be a single compound or a mixture of compounds having at least two hydroxyl groups selected from a group consisting of 1,3-butanediol, 1,4-butanediol, 1,5-pentanediol, 1,6-hexanediol, neopentylglycol, propyleneglycol, ethyleneglycol, polyethyleneglycol (MW: 200~2,000), glycerol, trimethylolethane, trimethylolpropane, pentaerythritol, sorbose and sorbitol. In particular, glycerol, sorbitol, polyethyleneglycol (MW: 200~2,000) and trimethylolpropane are more preferred.

The surfactant is one or more compounds selected from a group consisting of ethyleneoxide/propyleneoxide copolymers such as L-62, L-64, P-84, P-85, P-105, F-68, F-87, F-88, F-108, F-127 or a mixture thereof (Basf, Germany), and silicon-based surfactants such as L-508, L-5305, L-5302 and L-3150 (Osi).

As an adjuvant, a moisturizing agent and a wound healing accelerator, a pigment, an antimicrobial agent, and a growth factor can be added.

The moisturizing agent and the wound healing accelerator herein can be one or more compounds selected from a group consisting of high-absorptive polymers and natural substances such as polyacrylic acid, polyvinylalcohol, polyoxyethylene, polyethyleneoxide, polysaccharide, polymethacrylic acid, polyacrylamide, polyethyleneoxide, cellulose, carboxymethylcellulose, pectin, guar gum, sodiumalginate, chitin, chitosan, gelatin, starch, hyaluronic acid, keratan, collagen, dermatansulfate, sodiumcarboxymethylcellulose, locust bean gum, hydroxyethylcellulose, xanthan gum, pulp and karaya gum.

The antimicrobial agent used in the present invention can be selected from a group consisting of gluconate chlorohexidine, acetate chlorohexidine, hydrochloride chlorohexidine, silversulfurdiazine, povidone iodine, benzalkonium chloride, furagin, idokine, hexachlorophene, chlorotetracycline, neomycin, penicillin, gentamycin or acrinol.

The growth factor of the present invention can be one or more compounds selected from a group consisting of PDGF, TGF-$\beta$, EGF, FGF and VEGF.

The protective layer (20) of the present invention is a waterproof breather film 10~300 μm thick, which is laminated directly on the wound contact layer (10) having a sponge structure, or indirectly laminated over the adhesive layer.

The tensile strength of the protective layer (20) is 45~700 kg and the elasticity is preferably 200~1,000%.

The present invention is described in detail hereinafter with reference to the following figures.

FIG. 1 is a sectional diagram illustrating the polyurethane foam dressing material of the present invention. The polyurethane foam dressing material of the present invention has a double layer structure composed of the wound contact layer (10) and the protective layer (20). The protective layer (20) is a film 10~300 μm thick with a water vapor permeability of 200~1,500 g/m²-day. The protective layer (20) has a non-porous structure to prevent the invasion of foreign materials. Various films can be used as the protective layer (20) but polyurethane film is preferred. Various types of polyurethane can be used for the film and an adhesive polyurethane film which is prepared by coating a polyurethane film with an adhesive can also be used. In addition, natural rubber or other synthetic polymer films can be used, and in this case the film is preferably a thin, soft film having a water vapor permeability of 200~1,500 g/m²-day.

The wound contact layer (10) is composed of open cells (12) 50~300 μm in mean diameter, and pores (15) 5~85 μm in mean diameter which make a tunnel between the open cells (12). The open cells (12) take 20~80% of the total area to form a sponge like structure therein.

The wound contact layer has high density of 0.15~0.45 g/cm³ and high water absorptiveness of 400~2,000 weight %.

FIG. 2 is a photograph (×100) from a scanning electron microscope (SEM) of the wound contact layer (10) prepared in Example 1, which is easily distinguishable from SEM photographs of the prior art or other products.

FIG. 3 is a photograph from a scanning electron microscope (×100) of the section of the contact layer (absorption layer and contact layer combined) described in Korean Patent No. 553078. FIG. 4a and FIG. 4b are photographs from a scanning electron microscope (×100) of the absorption layer (a) and the wound contact layer (b) described in U.S. Pat. No. 5,445,604. FIG. 5a and FIG. 5b are photographs from a scanning electron microscope (×100) of the absorption layer (a) and the wound contact layer (b) described in U.S. Pat. No. 5,064,653.

As shown in the figures, the wound contact layer (10) of the present invention, in which the absorption layer and the contact layer are combined, is expected to maintain a high moisturizing rate because the cells are smaller and more packed therein. However, the wound contact layer and the absorption layer according to the U.S. Pat. No. 5,445,604 and No. 5,064,653 have bigger porous cells, resulting in a decrease of the moisturizing rate, in addition to causing the adhesion of the wound contact layer to the wounded area owing to its big pores.

BRIEF DESCRIPTION OF THE DRAWINGS

The application of the preferred embodiments of the present invention is best understood with reference to the accompanying drawings, wherein.

Figure 1:
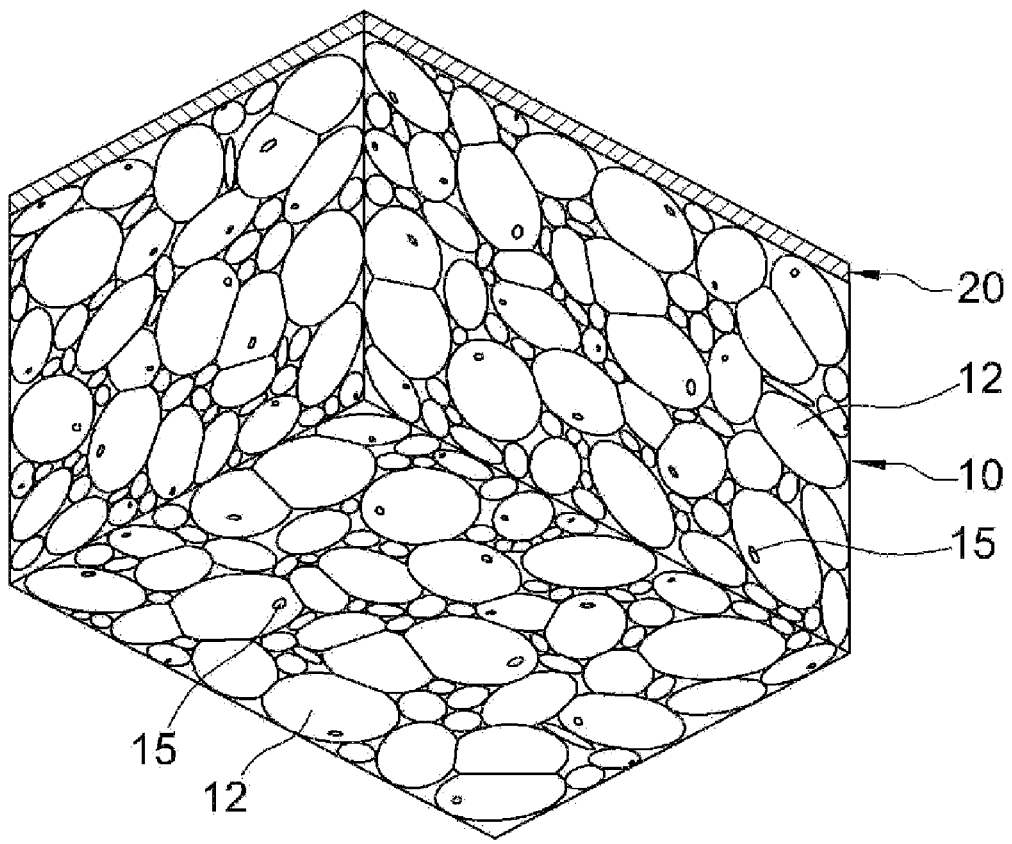
FIG. 1 is a sectional diagram of the polyurethane foam dressing material of the present invention.

| 10: Wound contact layer | 12: Open cell |
| 15: Pore | 20: Protective layer |

BEST MODE FOR CARRYING OUT THE INVENTION

Practical and presently preferred embodiments of the present invention are illustrated as shown in the following examples.

However, it will be appreciated that those skilled in the art, on consideration of this disclosure, may make modifications and improvements within the spirit and scope of the present invention.

SYNTHETIC EXAMPLE 1

Polyurethane Prepolymer of the Wound Contact Layer

To a 3 liter round bottom flask equipped with a stirrer were added 354 g of diphenylmethanediisocyanate and 314 g of isophoronediisocyanate. The temperature was raised to 60°

C. and then ethyleneoxide/propyleneoxide random copolymer having at least 2 hydroxyl groups was added drop by drop, followed by reaction until the theoretical NCO % reached 12 to give a polyurethane prepolymer having an isocyanate terminal group. In the middle of the reaction, a sample was taken and the NCO % was measured by a titrimetric method using n-butylamine standard solution.

SYNTHETIC EXAMPLE 2

Polyurethane Prepolymer of the Wound Contact Layer

To a 3 liter round bottom flask equipped with a stirrer were added 296 g of diphenylmethanediisocyanate and 275 g of isophoronediisocyanate. The temperature was raised to 60° C. and then ethyleneoxide/propyleneoxide random copolymer having at least 2 hydroxyl groups was added drop by drop, followed by reaction until the theoretical NCO % reached 5 to give a polyurethane prepolymer having an isocyanate terminal group. In the middle of the reaction, a sample was taken and the NCO % was measured by a titrimetric method using n-butylamine standard solution.

EXAMPLE 1

To 66.85 weight % of the polyurethane prepolymer prepared in the above Synthetic Example 2 were added 20.5 weight % of distilled water as a foaming agent, 10 weight % of glycerin as a cross-linking agent, 0.5 weight % of F-87 (Basf) as an additive, 0.05 weight % of L-64, 2 weight % of sodiumalginate, 0.05 weight % of silver sulfadiazine, and 0.05 weight % of a soluble pigment, followed by stirring at 4,000 rpm for 5 seconds. The mixture was poured in the mold of a certain shape and foamed. The temperature of the mold was set at 25° C. and separation was performed 10 minutes after the pouring. The skin layer was eliminated by using a horizontal splitting machine and the rest was cut into 5 mm thick sheets. One side of the polyurethane foam was heat-pressed with a polyurethane film to give a foam dressing material. The density of the hydrophilic polyurethane foam dressing material of the present invention was 0.25 g/cm$^3$.

FIG. 1 is a photograph from a scanning electron microscope (SEM) illustrating the polyurethane foam dressing material prepared in Example 1, and the physical properties thereof were measured as follows, with the results shown in Table 1.

① Mechanical Properties (Tensile Strength, Elongation, Modulus)

Mechanical properties were measured by ASTM D638-02 with Universal Test Machine (Instron, USA).

② Water Absorptiveness

The hydrophilic polyurethane foam dressing material was cut into 3 cm×3 cm pieces and dried in a 50° C. vacuum oven for 24 hours. Then, the initial weight (A) of a section was measured, and then the section was dipped in 25° C. distilled water for 4 hours. The moisture on the surface of the sample was dried with tissue and then the weight of the sample was measured (B). Water absorptiveness was calculated by the following formula.

Water absorptiveness (%)=(B−A)/A×100

③ Moisturizing Rate

The hydrophilic polyurethane foam dressing material was cut into 3 cm×3 cm pieces and dried in a 50° C. vacuum oven for 24 hours. Then, the initial weight (A) of a section was measured, and then the section was dipped in 25° C. distilled water for 4 hours. A 3 kg roller was rolled three times on the sample and then the weight of the sample was measured (C). Then, the moisturizing rate was calculated by the following formula.

Moisturizing rate (%)=(C−A)/A×100

④ Sizes and Percentages of the Cells and the Pores

Exudation absorption depends not only on the hydrophilicity of the foam itself but also on the sizes of the cells and the pores therein. That is, the size and the percentage of the cells and the pores primarily affect the capillary phenomenon per unit area to change the absorption speed and absorption capacity, and secondarily affect the moisturizing capacity, which results in a big difference in exudation absorption capacity and the maintenance of humid conditions.

The sizes of the cells and the pores can be measured by mercury intrusion porosimetry with a porosimeter, but a scanning electron microscope (SEM) is generally used. Thus, in the present invention, an SEM was used to measure the sizes and the percentages of the cells and the pores of the hydrophilic polyurethane foam dressing material.

⑤ Wound Healing Effect

To examine the wound healing effect of the hydrophilic polyurethane foam dressing material, rats (6~8 weeks old, 250~300 g) were used. After anesthetizing the rat by an intra-abdominal injection of Nembutal, the skin on the back was cut to make a 4×4 cm wound, followed by dressing. After dressing, the changes of the area of the skin defect were observed over time at weekly intervals, and detachment of the tissues during dressing change was also investigated. Also, a histological test was performed to determine the wound healing effect of the dressing.

COMPARATIVE EXAMPLE 1

To 39.5 weight % of the polyurethane prepolymer prepared in Synthetic Example 1 were added 35.5 weight % of distilled water as a foaming agent, 22.5 weight % of glycerin as a cross-linking agent, 0.5 weight % of F-108 (Basf) as a surfactant and 2 weight % of sodiumalginate. The mixture was poured in a mold of a certain shape and foamed. The temperature of the mold was set at 25° C. and separation was performed 10 minutes after the pouring. The skin layer was eliminated by using a horizontal splitting machine and the rest was cut into a 5 mm thick sheet. One side of the polyurethane foam was heat-pressed with a polyurethane film to give a foam dressing material. The density of the hydrophilic polyurethane foam dressing material of the present invention was 0.27 g/cm$^3$. The physical properties of the dressing material were measured in the same manner as described in Example 1, and the results are shown in Table 1.

COMPARATIVE EXAMPLE 2

A polyurethane foam dressing material was prepared in the same manner as described in Example 1, except that a smaller amount of the foaming solution was poured in the mold than Example 1 and thus the density of this polyurethane foam dressing material was 0.13 g/cm$^3$. The physical properties of the dressing material were measured in the same manner as described in Example 1, and the results are shown in Table 1.

COMPARATIVE EXAMPLE 3

A polyurethane foam dressing material was prepared in the same manner as described in Example 1, except that a smaller amount of foaming solution was poured in the mold than Example 1 and thus the density of this polyurethane foam dressing material was 0.5 g/cm³. The physical properties of the dressing material were measured in the same manner as described in Example 1, and the results are shown in Table 1.

COMPARATIVE EXAMPLE 4

To 75.35 weight % of the polyurethane prepolymer prepared in Synthetic Example 2 were added 10 weight % of distilled water as a foaming agent, 12 weight % of glycerin as a cross-linking agent, 0.5 weight % of F-87 (Basf) as an additive, 0.05 weight % of L-64, 2 weight % of sodiumalginate, 0.05 weight % of silver sulfadiazine and 0.05 weight % of a soluble pigment, followed by stirring at 4,000 rpm for 5 seconds. The mixture was poured in a mold of a certain shape and foamed. The temperature of the mold was set at 25° C. and separation was performed 10 minutes after the pouring. The skin layer was eliminated by using a horizontal splitting machine and the rest was cut into a 5 mm thick sheet. One side of the polyurethane foam was heat-pressed with a polyurethane film to give a foam dressing material. The density of the hydrophilic polyurethane foam dressing material of the present invention was 0.25 g/cm³.

Figure 2:
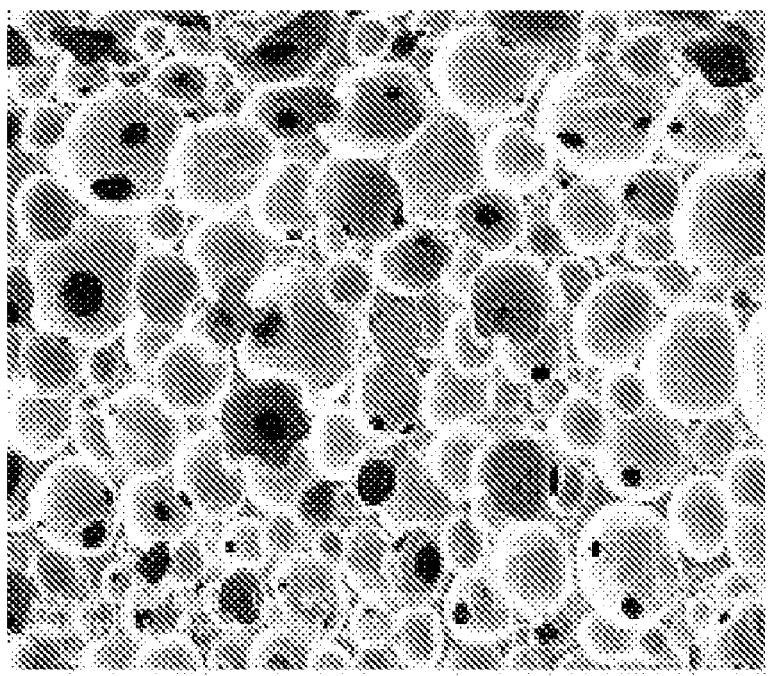
FIG. 2 is a photograph from a scanning electron microscope of a section of the contact layer of the polyurethane foam dressing material prepared by the method of the present invention.
Figure 3:
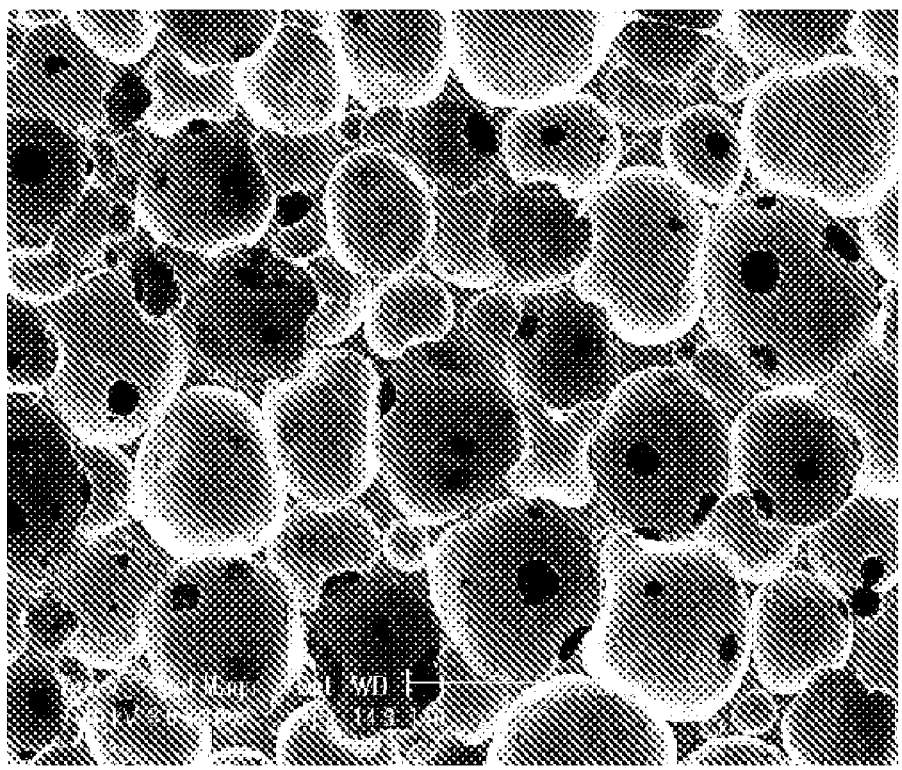
FIG. 3 is a photograph from a scanning electron microscope of a section of the contact layer described in Korean Patent No. 553078.
Figure 4A:
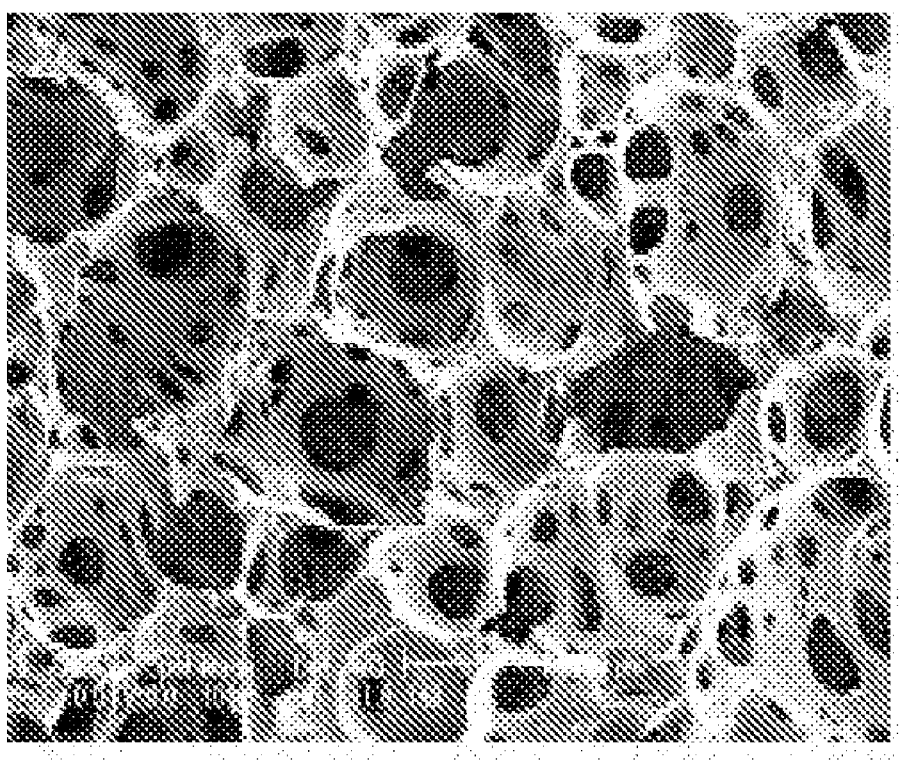
FIG. 4a and FIG. 4b are photographs from a scanning electron microscope of the absorption layer and the wound contact layer described in U.S. Pat. No. 5,445,604.
Figure 4B:
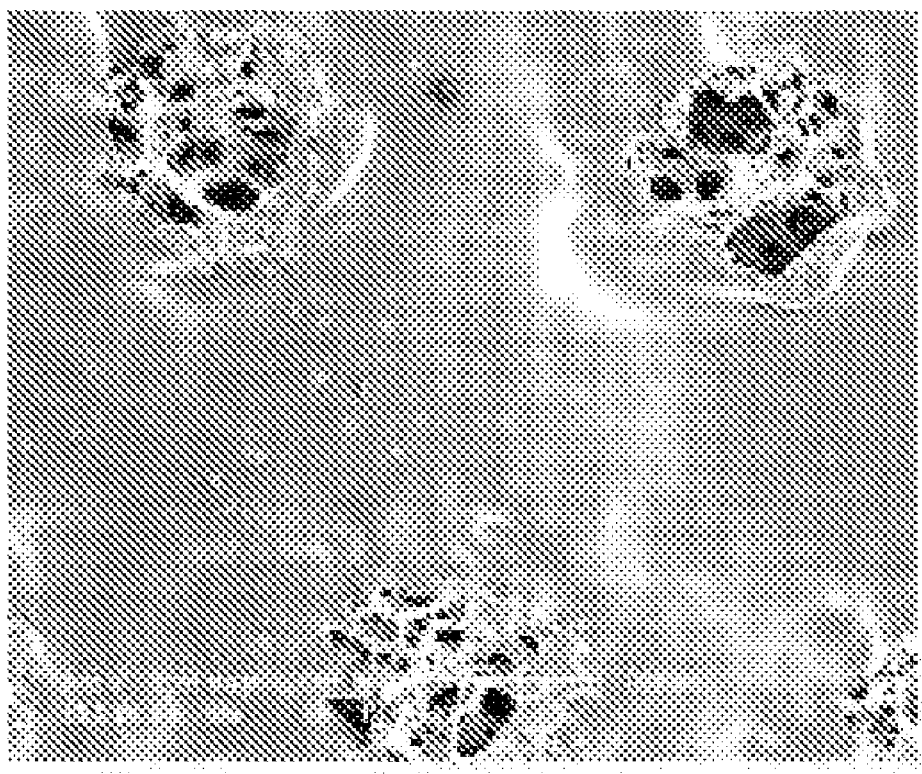
Figure 5A:
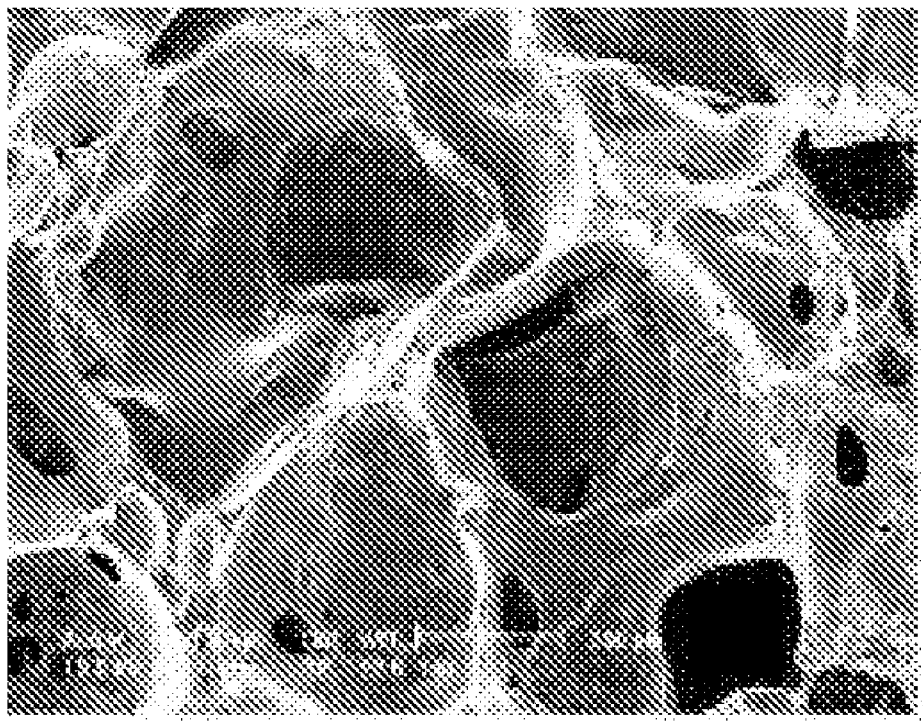
FIG. 5a and FIG. 5b are photographs from a scanning electron microscope of the absorption layer and the wound contact layer described in U.S. Pat. No. 5,064,653.
Figure 5B:
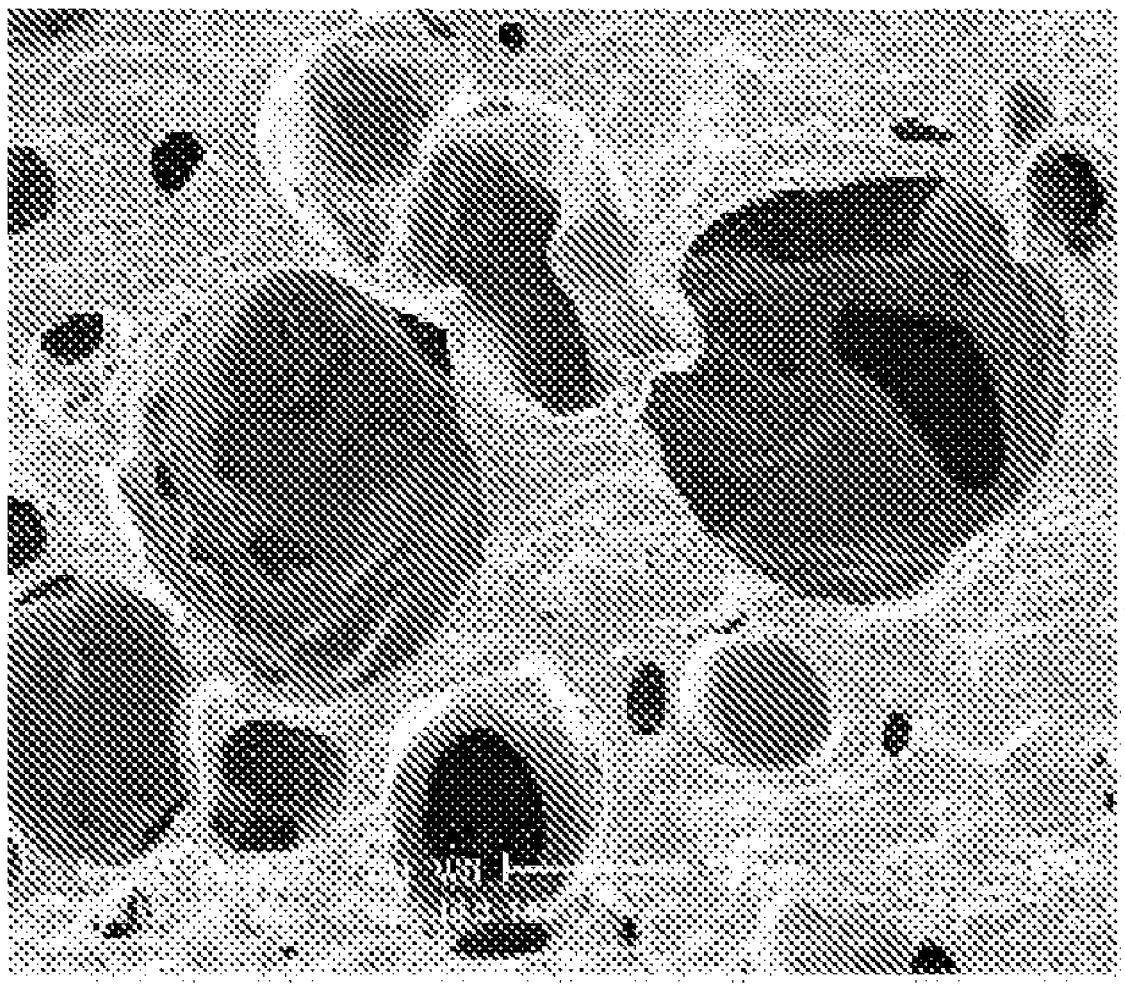

FIG. 2 is a photograph from a scanning electron microscope (SEM) of the polyurethane foam dressing material prepared in Example 1; the physical properties thereof were measured and the results are shown in Table 1.

INDUSTRIAL APPLICABILITY

As explained hereinbefore, the polyurethane foam dressing material of the present invention has the advantages of preventing the invasion of foreign materials, releasing absorbed exudation in the form of water vapor or keeping the exudation inside the foam to maintain the desired humidity, excellent exudation absorption and non-adhesion of the wound contact layer, ease of dressing change, increased moisturizing rate to provide optimum humidity, and thereby promoting a wound healing effect.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method for preparing a two layer hydrophilic polyurethane foam dressing material with improved moisturizing rate, said method comprising laminating a wound contact layer (10), having a sponge structure composed of multiple

TABLE 1

[Physical properties of the hydrophilic polyurethane foam dressing material]

|  | Tensile strength (gf/mm²) | Elongation (%) | Mean diameter of open cells (μm) | Ratio of open cells (%) | Mean diameter of pores (μm) | Ratio of pore area (%) | Water absorptiveness (%) | Moisturizing rate (%) | Wound healing effect |
|---|---|---|---|---|---|---|---|---|---|
| Example 1 | 22 | 620 | 200 | 50 | 65 | 20 | 1,530 | 1,050 | ◉ |
| Comparative Example 1 | 27 | 670 | 550 | 85 | 152 | 65 | 1,750 | 215 | X |
| Comparative Example 2 | 25 | 640 | 485 | 74 | 95 | 62 | 1,620 | 285 | Δ |
| Comparative Example 3 | 23 | 620 | 47 | 28 | 12 | 8.5 | 620 | 560 | Δ |
| Comparative Example 4 | 23 | 635 | 250 | 30 | 45 | 9.5 | 740 | 510 | Δ |

◉: Very good,
○: Good,
Δ: Not bad,
X: Bad

As shown in Table 1, the density of the polyurethane foam dressing material and the mixing ratio of the foaming solution affected the mean diameter of the open cells (12), the ratio of the open cells, the mean diameter of the pores, the ratio of pore area, the water absorptiveness, and the moisturizing rate. The mean diameter of the open cells (12), the ratio of the open cells, the mean diameter of the pores and the ratio of pore area also affect the water absorptiveness and the moisturizing rate, suggesting that they are the factors regulating the wound healing effect of the dressing material. The tensile strength and the elongation of the polyurethane foam were confirmed to be consistent with those of a protective film adhered on the wound contact layer by heat-pressing, indicating that the protective film layer affects the physical properties of the final product.

open cells (12) and pores (15) passing through the cells (12), with a protective film (20) at 150~250° C. under a pressure of 0.25~1 kgf/cm², wherein said laminating is by heat-press;

wherein the wound contact layer (10) has a moisturizing rate of 510~1050% and the pore area (membrane opening) takes 10~20% of the total cell area;

wherein the mean diameter of the open cells (12) is 50~300 μm and the mean diameter of the pores (15) is 5~85 μm;

wherein the ratio of the open cells to the wound contact layer (10) is 30~50%;

wherein the wound contact layer (10) has a density of 0.15~0.45 g/cm³; and wherein the wound contact layer (10) has a water absorptiveness of 700~1800 weight %.

2. The method for preparing a hydrophilic polyurethane foam dressing material with improved moisturizing rate according to claim 1, wherein the wound contact layer (10) is prepared by the steps of: mixing 40~70 weight % of a polyurethane prepolymer with 15~45 weight % of a foaming agent, 5~35 weight % of a cross-linking agent, 0.1~2 weight % of a surfactant and 0.5~15 weight % of an adjuvant with stifling; pour-foaming the mixture in the mold to prepare a polyurethane foam; and slicing thereof.

3. The method for preparing a hydrophilic polyurethane foam dressing material with improved moisturizing rate according to claim 2, wherein the surfactant is one or more compounds selected from a group consisting of ethyleneoxide/propyleneoxide copolymers or a mixture thereof and silicon-based surfactants.

4. The method for preparing a hydrophilic polyurethane foam dressing material with improved moisturizing rate according to claim 2, wherein the adjuvant is one or more compounds selected from a group consisting of a moisturizing and wound healing accelerator, a pigment, an antimicrobial agent, and a growth factor.

5. The method for preparing a hydrophilic polyurethane foam dressing material with improved moisturizing rate according to claim 4, wherein the moisturizing and wound healing accelerator is one or more compounds selected from a group consisting of high-absorptive polymers and natural substances such as polyacrylic acid, polyvinylalcohol, polyoxyethylene, polyethyleneoxide, polysaccharide, polymethacrylic acid, polyacrylamide, polyethyleneoxide, cellulose, carboxymethylcellulose, pectin, guar gum, sodium alginate, chitin, chitosan, gelatin, starch, hyaluronic acid, keratin, collagen, dermatan sulfate, sodium carboxymethylcellulose, locust bean gum, hydroxyethylcellulose, xanthan gum, pulp and karaya gum.

6. The method for preparing a hydrophilic polyurethane foam dressing material with improved moisturizing rate according to claim 4, wherein the antimicrobial agent is selected from a group consisting of gluconate chlorohexidine, acetate chlorohexidine, hydrochloride chlorohexidine, silver sulfurdiazine, povidone iodine, benzalkonium chloride, furagin, idokine, hexachlorophene, chlorotetracycline, neomycin, penicillin, gentamycin and acrinol.

7. The method for preparing a hydrophilic polyurethane foam dressing material with improved moisturizing rate according to claim 4, wherein the cell growth factor is one or more selected from a group consisting of PDGF, TGF-β, EGF, FGF and VEGF.

8. The method for preparing a hydrophilic polyurethane foam dressing material with improved moisturizing rate according to claim 1, wherein the protective layer (20) is a waterproof breather film 10~300 μm thick, which is laminated on the wound contact layer (10) having a sponge structure.

9. The method for preparing a hydrophilic polyurethane foam dressing material with improved moisturizing rate according to claim 1, wherein the protective layer (20) has a tensile strength of 45~700 kg and an elongation of 200~1,000%.

* * * * *